(12) United States Patent
Teng et al.

(10) Patent No.: US 9,244,083 B2
(45) Date of Patent: Jan. 26, 2016

(54) COMPOSITIONS AND METHODS FOR DETECTING VITAMIN D

(71) Applicants: Zhu Teng, Garnet Valley, PA (US); Roland Janzen, Hockessin, DE (US); Martin A. Drinan, Newark, DE (US)

(72) Inventors: Zhu Teng, Garnet Valley, PA (US); Roland Janzen, Hockessin, DE (US); Martin A. Drinan, Newark, DE (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 325 days.

(21) Appl. No.: 13/690,332

(22) Filed: Nov. 30, 2012

(65) Prior Publication Data
US 2014/0154700 A1    Jun. 5, 2014

(51) Int. Cl.
*G01N 33/532* (2006.01)
*G01N 33/82* (2006.01)
*C07C 401/00* (2006.01)
*A61K 39/385* (2006.01)

(52) U.S. Cl.
CPC .............. *G01N 33/82* (2013.01); *C07C 401/00* (2013.01); *A61K 39/385* (2013.01); *G01N 33/532* (2013.01); *Y10T 436/203332* (2015.01)

(58) Field of Classification Search
CPC ..... G01N 33/82; G01N 33/532; C07K 16/44; A61K 39/385; C07C 401/00
See application file for complete search history.

(56) References Cited

U.S. PATENT DOCUMENTS

| | | | |
|---|---|---|---|
| 4,456,553 A | 6/1984 | Oshida et al. | |
| 4,816,417 A | 3/1989 | DeLuca et al. | |
| 5,075,465 A | 12/1991 | Nakagawa et al. | |
| 5,093,519 A | 3/1992 | Bouillon et al. | |
| 5,786,347 A | 7/1998 | Hesse et al. | |
| 5,821,020 A | 10/1998 | Hollis | |
| 5,981,779 A | 11/1999 | Holick et al. | |
| 6,291,693 B1 | 9/2001 | Holick et al. | |
| 6,787,660 B1 | 9/2004 | Armbruster et al. | |
| 6,929,797 B2 | 8/2005 | Mazess et al. | |
| 7,087,395 B1 | 8/2006 | Garrity et al. | |
| 7,482,162 B2 | 1/2009 | Lauric et al. | |
| 7,632,929 B2 * | 12/2009 | Owens et al. | 530/403 |
| 7,745,226 B2 | 6/2010 | Clarke et al. | |
| 8,133,694 B2 | 3/2012 | Armbruster et al. | |
| 8,173,442 B2 | 5/2012 | Holmquist et al. | |
| 2004/0132104 A1 | 7/2004 | Sackrison et al. | |
| 2005/0014211 A1 | 1/2005 | Armbruster et al. | |
| 2008/0317764 A1 | 12/2008 | Huber et al. | |

(Continued)

FOREIGN PATENT DOCUMENTS

| | | |
|---|---|---|
| EP | 0583945 A2 | 2/1994 |
| WO | 02057797 A2 | 7/2002 |

(Continued)

OTHER PUBLICATIONS

J. Freeman, et al., Development of the ADVIA Centaur(R) Systems Vitamin D Total Assay, Clinical Chemistry, vol. 56, No. 6, Supplement, 2010, p. A153-154.

(Continued)

*Primary Examiner* — Shafiqul Haq
(74) *Attorney, Agent, or Firm* — Theodore J. Leitereg

(57) ABSTRACT

Compounds include carbamate derivatives of vitamin D including vitamin $D_3$ and vitamin $D_2$. The compounds are useful in methods and kits for determining the presence and/or amount of vitamin D including vitamin D analogs and metabolites thereof in a sample suspected of containing the same.

3 Claims, 2 Drawing Sheets

(56) References Cited

U.S. PATENT DOCUMENTS

| | | | |
|---|---|---|---|
| 2009/0093445 A1 | 4/2009 | Kyriatsoulis et al. | |
| 2012/0094396 A1 | 4/2012 | Petkovich et al. | |

FOREIGN PATENT DOCUMENTS

| | | | |
|---|---|---|---|
| WO | 2004063704 A2 | 7/2004 | |
| WO | 2007039193 A1 | 4/2007 | |
| WO | 2007039194 A1 | 4/2007 | |
| WO | WO 2007039193 A1 * | 4/2007 | |
| WO | 2007140962 A2 | 12/2007 | |
| WO | 2012104643 A1 | 8/2012 | |
| WO | 2012136720 A1 | 10/2012 | |

OTHER PUBLICATIONS

International Search Report and Written Opinion of International Application No. PCT/IB2013/002934 mailed on May 14, 2014.

* cited by examiner

COMPOSITIONS AND METHODS FOR DETECTING VITAMIN D

BACKGROUND

This invention relates to compositions, methods and kits for determining the presence and/or amount of vitamin D including vitamin D analogs and metabolites thereof in a sample suspected of containing the same.

The term "vitamin D" refers to a group of fat-soluble secosteroids. In humans, vitamin D is unique because it can be ingested as cholecalciferol (vitamin $D_3$) or ergocalciferol (vitamin $D_2$) and because the body can also synthesize it (from cholesterol) when sun exposure is adequate. Because of this latter property, vitamin D is considered by some to be a non-essential dietary vitamin although most consider it an essential nutrient. Vitamin D has an important physiological role in the positive regulation of calcium ion homeostasis. Vitamin $D_3$ is the form of the vitamin synthesized by animals. It is also a common supplement added to milk products and certain food products as is vitamin $D_2$.

Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxycholecalciferol (also referred to as calcidiol, calcifediol, 25-hydroxycholecalciferol, or 25-hydroxyvitamin D (abbreviated 25(OH)D). The latter compound, i.e., 25-hydroxyvitamin D, is the specific vitamin D metabolite that is measured in serum to determine vitamin D status. Calcidiol is the major form of Vitamin $D_3$ in the circulatory system. Circulating calcidiol is converted by the kidney to 1,25-dihydroxyvitamin $D_3$ (calcitriol; 1,25(OH)$_2$D$_3$), which is believed to be the most biologically active form of vitamin D.

Assessing vitamin D levels in biological samples is important since vitamin D deficiency is related to a number of disorders in mammals. There is a need for reagents and methods for accurate and sensitive determinations of concentrations of vitamin D, vitamin D analogs and metabolites thereof in samples.

SUMMARY

Some examples in accordance with the principles described herein are directed to a compound of the formula:

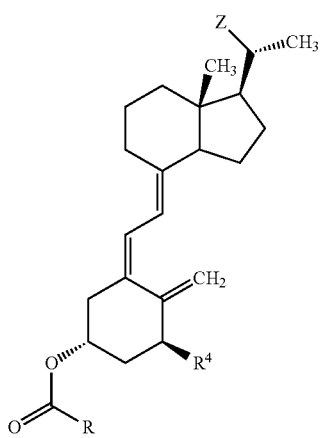

wherein:

Z is an alkyl, alkenyl or alkynyl group having 1 to 10 carbon atoms, which may be unsubstituted or one or more of which may be substituted by one or more of hydroxy, lower alkoxy, oxo and oxime;

R is —O-succinimidyl, —NH—O-(A)$_k$-R$^2$, wherein R$^2$ is a member of a signal producing system, —(CH$_2$)$_n$COOH, —(CH$_2$)$_m$COONHS (NHS is N-hydroxysuccinimide), a small molecule, a binding partner for a small molecule, or a support; A is a linking group; k is 0 or 1; n is an integer of 1 to 5 and m is an integer of 1 to 5; and R$^4$ is H, OH or lower alkoxy.

Some examples in accordance with the principles described herein are directed to a compound of the formula:

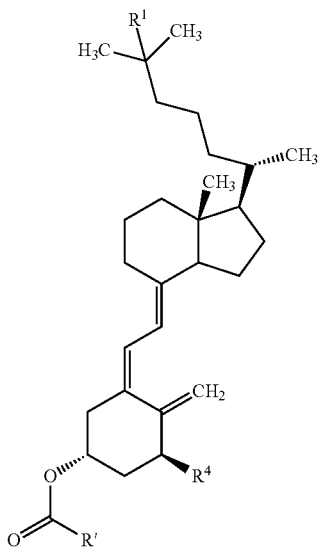

or a compound of the formula:

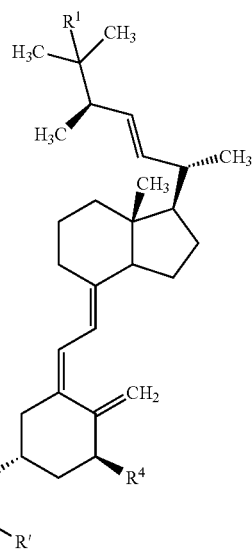

wherein:

R' is —O-succinimidyl or —NH—O-(A)$_k$-R$^2$, wherein R$^2$ is a member of a signal producing system, —(CH$_2$)$_n$COOH, —(CH$_2$)$_m$COONHS (NHS is N-hydroxysuccinimide), a small molecule, a binding partner for a small molecule, or a support; A is a linking group; k is 0 or 1; n is an integer of 1 to 5 and m is an integer of 1 to 5;

$R^1$ is H, OH, or protected OH; and $R^4$ is H, OH or lower alkoxy.

Some examples in accordance with the principles described herein are directed to a compound of the formula:

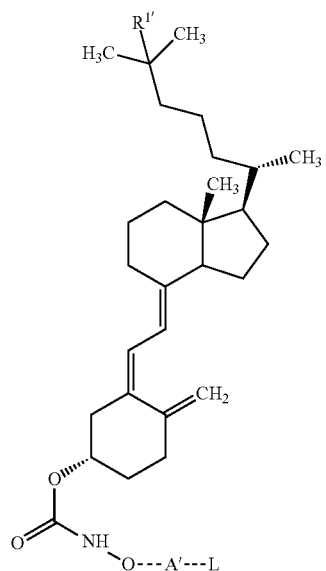

or a compound of the formula:

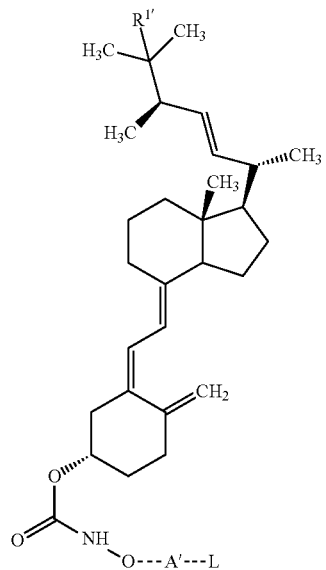

wherein:

L is selected from the group consisting of chemiluminescent particles and sensitizer particles and $R^{1'}$ is OH and A' is a linking group.

Some examples in accordance with the principles described herein are directed to methods of determining one or both of the presence and the amount of vitamin D in a sample suspected of containing vitamin D. In the method a combination in a medium is provided that comprises the sample, a compound as described above and a specific binding member for vitamin D. The combination is subjected to conditions for binding of the compound to the specific binding member to form a complex. The amount of the complex is measured where the amount of the complex is related to one or both of the presence and amount of vitamin D in the sample.

Some examples in accordance with the principles described herein are directed to methods of determining one or both of the presence and the amount of vitamin D in a sample suspected of containing vitamin D. A combination is provided that comprises the sample, a specific binding member for vitamin D and a compound of the formula:

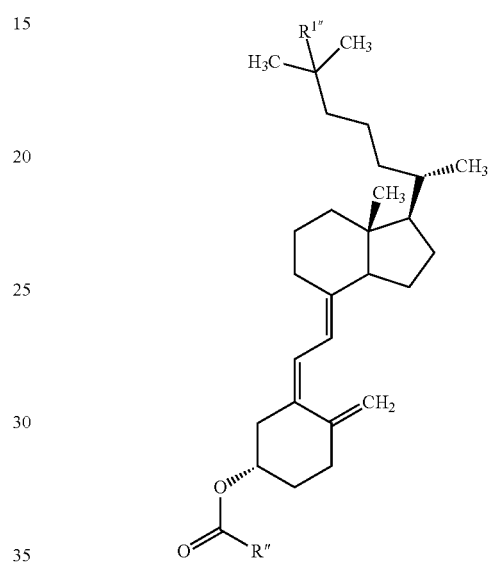

or a compound of the formula:

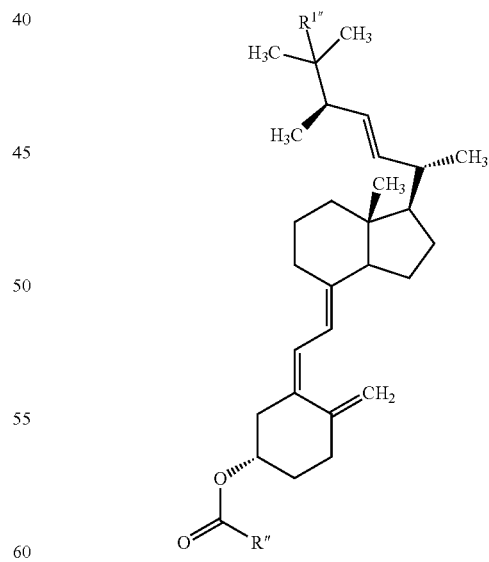

wherein:

R" is —NH—O-A"—$R^{2'}$, wherein $R^{2'}$ is a member of a signal producing system and A" is a linking group, and $R^{1''}$ is H or OH.

The combination is subjected to conditions for binding of the compound to the specific binding member to form a complex, and the amount of the complex is measured. The amount of the complex is related to the presence and/or amount of vitamin D in the sample.

DETAILED DESCRIPTION OF SPECIFIC EMBODIMENTS

Compounds

Figure 1:
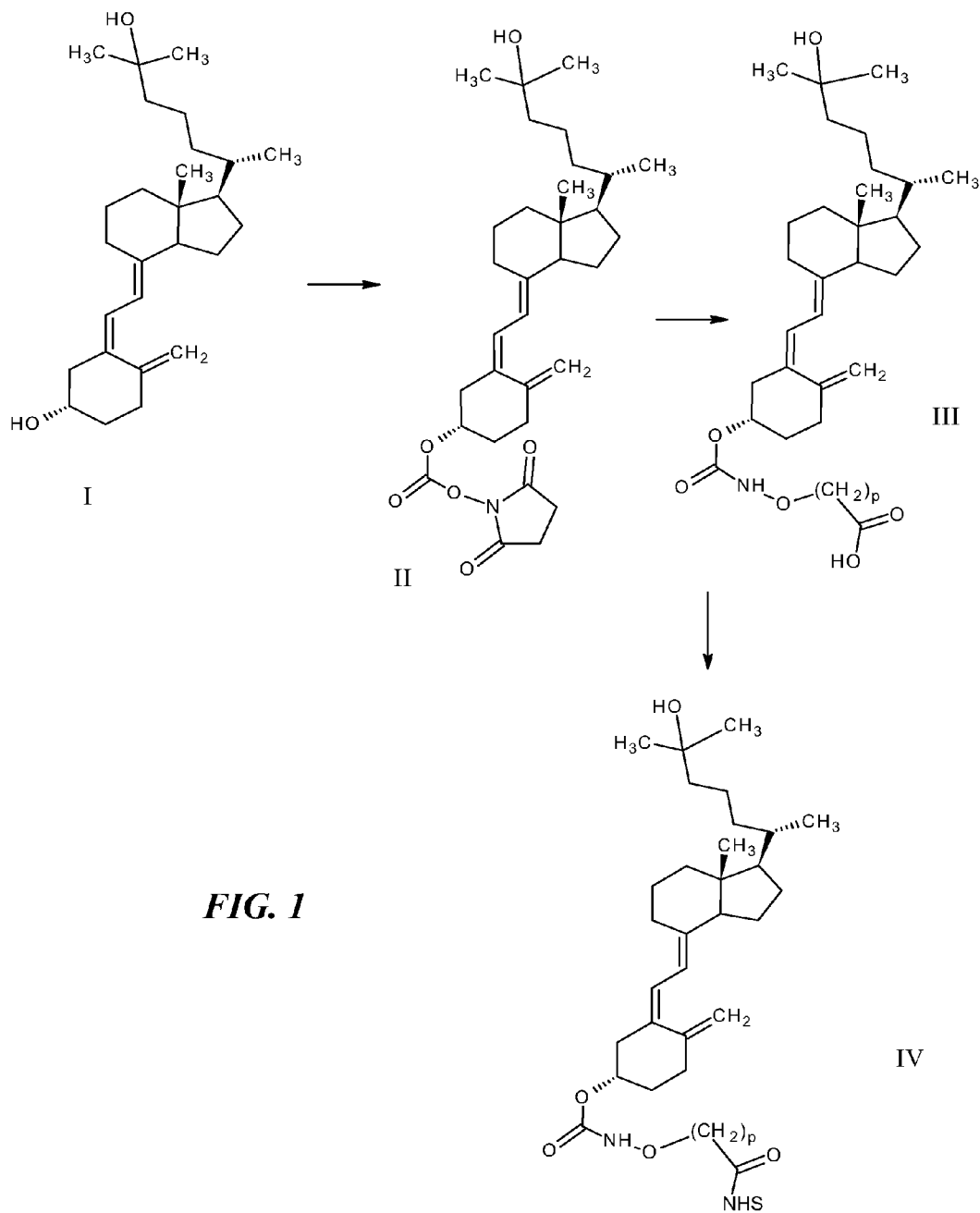
FIG. 1 is a schematic diagram of a synthesis of compounds in accordance with examples in accordance with the principles described herein.

As mentioned above, some examples in accordance with the principles described herein are directed to compounds of the formula:

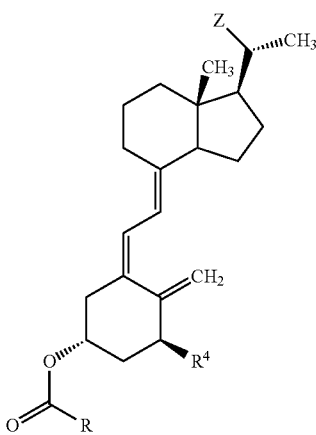

wherein:

Z is an alkyl, alkenyl or alkynyl group having, for example, 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, carbon atoms, which may be unsubstituted or one or more of which may be substituted by one or more of hydroxy, alkoxy of 1 to 5, or 1 to 4, of 1 to 3, or 1 to 2, or 2 to 5, or 2 to 4, or 2 to 3, or 3 to 5, or 3 to 4, or 4 to 5 carbon atoms, oxo, or oxime; and R is —O-succinimidyl or —NH—O-(A)$_k$-R$^2$, R$^2$ is a member of a signal producing system, —(CH$_2$)$_n$COOH, —(CH$_2$)$_m$COONHS (NHS is N-hydroxysuccinimide), a small molecule, a binding partner for a small molecule, or a support; A is a linking group; k is 0 or 1; n is an integer of 1 to 5, or 1 to 4, of 1 to 3, or 1 to 2, or 2 to 5, or 2 to 4, or 2 to 3, or 3 to 5, or 3 to 4, or 4 to 5 and m is an integer of 1 to 5, or 1 to 4, of 1 to 3, or 1 to 2, or 2 to 5, or 2 to 4, or 2 to 3, or 3 to 5, or 3 to 4, or 4 to 5; and R$^4$ is H, OH or lower alkoxy.

The term "alkyl" includes those alkyl groups of a designated number of carbon atoms of either a straight, branched, or cyclic configuration. Examples of "alkyl" include, but are not limited to, methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, for example.

The term "alkenyl" includes hydrocarbon chains of a specified number of carbon atoms of either a straight- or branched-configuration and at least one carbon-carbon double bond, which may occur at any point along the chain, examples of which include, but are not limited to, ethenyl, propenyl, butenyl, pentenyl, dimethyl pentenyl, for example.

The term "alkynyl" refers to a straight or branched chain hydrocarbon of a specified number of carbon atoms containing at least one carbon-carbon triple bond, including, but not limited to, ethynyl, 1-propynyl, 2-propynyl, 1-butynyl, and 2-butynyl, for example.

The term "alkoxy" includes alkyl groups of a designated number of carbon atoms of either a straight, branched or cyclic configuration wherein the alkyl group includes an ether oxygen for linking to a parent compound.

In some examples in accordance with the principles described herein, the linking group A has a molecular weight less than about 2000, or less than about 1500, or less than about 1000, or less than about 500, or less than about 300, or less than about 200, or less than about 150, for example. The linking group may comprise about 2 to about 200 atoms, or 4 to about 150 atoms, or about 5 to about 100 atoms, or about 5 to about 50 atoms, or about 5 to about 25 atoms, not counting hydrogen, and may comprise a chain of from 2 to about 100 atoms, or 3 to about 90 atoms, or about 4 to about 80 atoms, or about 5 to about 70 atoms, or about 10 to about 50 atoms, or about 10 to about 25 atoms, or about 5 to about 20 atoms, or about 5 to about 10 atoms, for example, each independently selected from the group consisting of carbon, oxygen, sulfur, nitrogen, and phosphorous. The number of heteroatoms in the linking group is dependent on the size of the linking group and, in some examples, the number is in the range of from 0 to about 30, or 1 to about 25, or about 2 to about 20, or about 2 to about 15, or about 2 to about 10, or about 3 to about 10, or about 3 to about 5, for example.

The heteroatoms may be in the form of one or more functionalities including, but not limited to, one or more of amine (primary, secondary or tertiary), carbamate, ether, ester, amide, urea, sulfonamide, thioether, hydrazone, hydrazide, amidine, and phosphate ester, for example. In one example in accordance with the principles described herein, the linking group comprises two nitrogen atoms in the form of secondary amine functionalities and one carbonyl group in a chain of about 6 to about 20, or about 6 to about 15, or about 6 to about 10, or about 7 to about 20, or about 7 to about 15, or about 7 to about 10, or about 7 to about 9, or about 7 to about 8, or about 7 atoms, which number of atoms includes carbon atoms.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-,β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed.

As mentioned above, in some examples in accordance with the principles described herein, $R^2$ may be a member of a signal producing system. The signal producing system may have one or more components, at least one component being a label. The signal producing system generates a signal that relates to the presence of vitamin D in a sample. The signal producing system includes all of the reagents required to produce a measurable signal. Other components of the signal producing system may be included in a developer solution and can include, but are not limited to, substrates, enhancers, activators, chemiluminescent compounds, cofactors, inhibitors, scavengers, metal ions, and specific binding substances required for binding of signal generating substances, for example. Other components of the signal producing system may be coenzymes, substances that react with enzymic products, other enzymes and catalysts, for example. The signal producing system provides a signal detectable by external means, by use of electromagnetic radiation, desirably by visual examination. Exemplary signal-producing systems are described in U.S. Pat. No. 5,508,178, the relevant disclosure of which is incorporated herein by reference.

The term "label" includes poly(amino acid) labels and non-poly(amino acid) labels. The term "poly(amino acid) label moieties" includes labels that are proteins such as, but not limited to, enzymes, antibodies, peptides, and immunogens, for example. With label proteins such as, for example, enzymes, the molecular weight range will be from about 10,000 to about 600,000, or from about 10,000 to about 300,000 molecular weight. There is usually at least one compound in accordance with the principles described herein (analog group) per about 200,000 molecular weight, or at least about 1 per about 150,000 molecular weight, or at least about 1 per about 100,000 molecular weight, or at least about 1 per about 50,000 molecular weight, for example, of the protein. In the case of enzymes, the number of analog groups is usually from 1 to about 20, about 2 to about 15, about 3 to about 12, or about 6 to about 10.

Enzymes include, by way of illustration and not limitation, redox enzymes such as, for example, dehydrogenases, e.g., glucose-6-phosphate dehydrogenase and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example.

The term "non-poly(amino acid) labels" includes those labels that are not proteins. The non-poly(amino acid) label is capable of being detected directly or is detectable through a reaction that produces a detectable signal. The non-poly (amino acid) label can be isotopic or non-isotopic and can be, by way of illustration and not limitation, a radioisotope, a luminescent compound (which includes, but is not limited to fluorescent compounds and chemiluminescent compounds, for example), a polynucleotide coding for a catalyst, a promoter, a dye, a coenzyme, an enzyme substrate, a radioactive group, and an amplifiable polynucleotide sequence, for example.

As mentioned above, in some examples in accordance with the principles described herein, $R^2$ may be a small organic molecule refers to a molecule of molecular weight of about 200 to about 2,000, or about 200 to about 1,500, or about 200 to about 1,000, or about 200 to about 500. Such small organic molecules include, but are not limited to, biotin, fluorescent molecules (such as fluorescein and rhodamine, for example), chemiluminescent molecules and dinitrophenol, for example. A binding partner for a small organic molecule is a molecule that specifically recognizes and binds to the small molecule. Binding partners for a small molecule are defined by the nature of the small molecule and include, but are not limited to, avidin, streptavidin, antibody for the small organic molecule (which include, but are not limited to, antibody for a fluorescent molecule (such as antibody for fluorescein and antibody for rhodamine, for example), antibody for a chemiluminescent molecule, antibody for dinitrophenol, for example.

As mentioned above, in some examples in accordance with the principles described herein, $R^2$ may be a support, which may be comprised of an organic or inorganic, solid or fluid, water insoluble material and which may be transparent or partially transparent. The support can have any of a number of shapes, such as, but not limited to, a particle (particulate support) including bead, a film, a membrane, a tube, a well, a strip, a rod, a fiber, or a planar surface such as, e.g., a plate or paper, for example. The support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as, by way of illustration and not limitation, nitrocellulose, cellulose acetate, poly (vinyl chloride), polyacrylamide, polyacrylate, polyethylene, polypropylene, poly (4 methylbutene), polystyrene, polymethacrylate, poly(ethylene terephthalate), nylon, poly(vinyl butyrate), for example, either used by themselves or in conjunction with other materials. The support may or may not be further labeled with a dye, catalyst or other detectable group, for example.

In some examples in accordance with the principles described herein, the support may be a particle. The particles have an average diameter of at least about 0.02 microns and not more than about 100 microns. In some examples, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus,* and *E. coli,* viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chromium dioxide (chrome) particles or latex particles.

In some examples in accordance with the principles described herein, Z in the above formula is —(CH$_2$)$_s$C(CH$_3$)$_2$-R$^1$ wherein s is an integer of 1 to 5, or 1 to 4, of 1 to 3, or 1 to 2, or 2 to 5, or 2 to 4, or 2 to 3, or 3 to 5, or 3 to 4, or 4 to 5, or 3, or 2, or 1, and R$^1$ is H, OH, or protected OH. In a particular example R$^1$ is OH. In a particular example in accordance with the principles described herein, s is 3 and the compound has the formula:

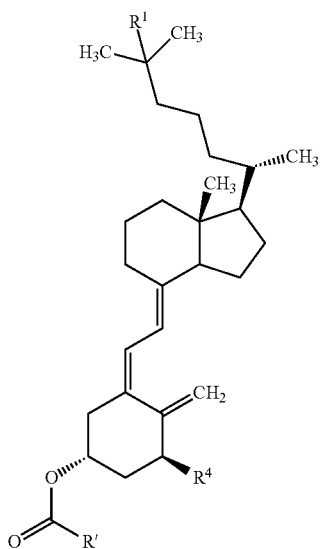

wherein:
R' is —O-succinimidyl or —NH—O-(A)$_k$-R$^2$, wherein R$^2$ is a member of a signal producing system, —(CH$_2$)$_n$COOH, —(CH$_2$)$_m$COONHS (NHS is N-hydroxysuccinimide), a small molecule, or a binding partner for a small molecule, a support, A is a linking group, k is 0 or 1, n is an integer of 1 to 5 and m is an integer of 1 to 5;

R$^1$ is H, OH, or protected OH. In a particular example, R$^1$ is OH; and

R$^4$ is H, OH or lower alkoxy. In a particular example, R$^4$ is H. In another particular example, R$^4$ is OH.

In some examples in accordance with the principles described herein, Z in the above formula is —(CH═CH) (CH$_2$)$_v$CH(CH$_3$)(CH$_3$)$_2$—R$^1$ wherein v is an integer of 0 to 5, or 0 to 4, of 0 to 3, or 0 to 2, or 0 to 1, or 1 to 5, or 1 to 4, of 1 to 3, or 1 to 2, or 2 to 5, or 2 to 4, or 2 to 3, or 3 to 5, or 3 to 4, or 4 to 5, or 3, or 2, or 1, and R$^1$ is H, OH, or protected OH. In a particular example R$^1$ is OH. In a particular example in accordance with the principles described herein, v is 0 and the compound has the formula:

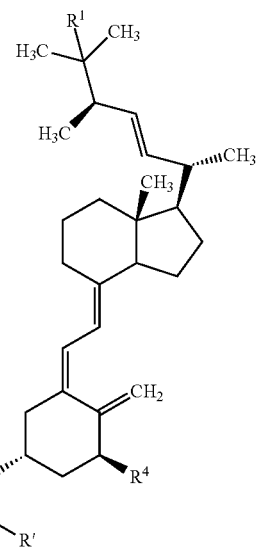

wherein:
R' is —O-succinimidyl or —NH—O-(A)$_k$-R$^2$, wherein R$^2$ is a member of a signal producing system, —(CH$_2$)$_n$COOH, —(CH$_2$)$_m$COONHS (NHS is N-hydroxysuccinimide), a small molecule, or a binding partner for a small molecule, a support, A is a linking group, k is 0 or 1, n is an integer of 1 to 5 and m is an integer of 1 to 5;

R$^1$ is H, OH, or protected OH. In a particular example, R$^1$ is OH; and

R$^4$ is H, OH or lower alkoxy. In a particular example, R$^4$ is H. In another particular example, R$^4$ is OH.

Some examples in accordance with the principles described herein are directed to derivatives of 25-OH vitamin D$_2$ and derivatives of 25-OH vitamin D$_3$ that comprise a carbamate linkage to another moiety either directly or through the intermediacy of a linking group. The moiety may be, but is not limited to, a member of a signal producing system, a support or a member of a specific binding pair.

In some examples in accordance with the principles described herein, the compound has the formula:

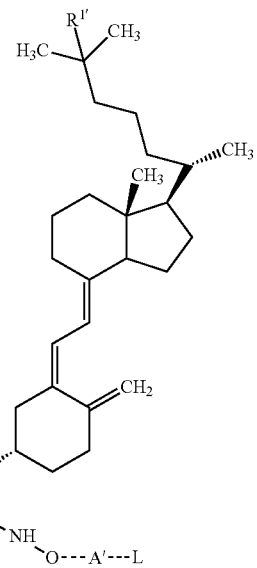

wherein:

L is selected from the group consisting of chemiluminescent particles and sensitizer particles and $R^{1'}$ is OH and A' is a linking group as described above. In some examples, the linking group has the formula —$(CH_2)_p$—C(O)—$(W)_b$—$(CH_2)_q$—$(X)_c$—$(CH_2)_r$— wherein W and X are each independently —NH— and —O—, b and c are each independently 0 or 1, p is an integer of 1 to 5, or 1 to 4, or 1 to 3, or 1 to 2, or 2 to 5, or 2 to 4, or 2 to 3, or 3 to 5, or 3 to 4, or 4 to 5, q is an integer of 1 to 5, or 1 to 4, or 1 to 3, or 1 to 2, or 2 to 5, or 2 to 4, or 2 to 3, or 3 to 5, or 3 to 4, or 4 to 5 and r is an integer of 1 to 5, or 1 to 4, or 1 to 3, or 1 to 2, or 2 to 5, or 2 to 4, or 2 to 3, or 3 to 5, or 3 to 4, or 4 to 5. In one example, b and c are each 1, p is 1, q is 2 and r is 1. In some examples, the linking group has the formula —$(CH_2)_p$—C(O)—NH—$(CH_2)_q$—NH—$(CH_2)_r$— wherein p, q and r are as defined above.

In some examples in accordance with the principles described herein, the compound has the formula:

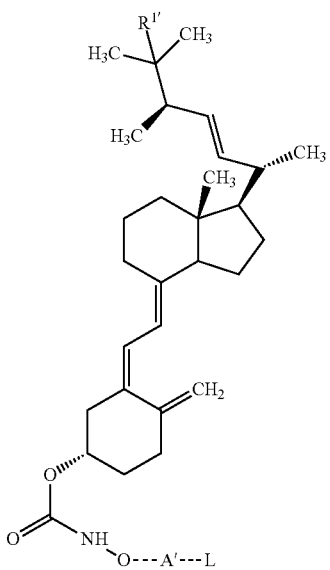

wherein:

L is selected from the group consisting of chemiluminescent particles and sensitizer particles and $R^{1'}$ is OH and A' is a linking group as described above. In some examples, the linking group has the formula —$(CH_2)_p$—C(O)—$(W)_b$—$(CH_2)_q$—$(X)_c$—$(CH_2)_r$— wherein W and X are each independently —NH— and —O—, b and c are each independently 0 or 1, p is an integer of 1 to 5, or 1 to 4, or 1 to 3, or 1 to 2, or 2 to 5, or 2 to 4, or 2 to 3, or 3 to 5, or 3 to 4, or 4 to 5, q is an integer of 1 to 5, or 1 to 4, or 1 to 3, or 1 to 2, or 2 to 5, or 2 to 4, or 2 to 3, or 3 to 5, or 3 to 4, or 4 to 5 and r is an integer of 1 to 5, or 1 to 4, or 1 to 3, or 1 to 2, or 2 to 5, or 2 to 4, or 2 to 3, or 3 to 5, or 3 to 4, or 4 to 5. In one example, b and c are each 1, p is 1, q is 2 and r is 1. In some examples, the linking group has the formula —$(CH_2)_p$—C(O)—NH—$(CH_2)_q$—NH—$(CH_2)_r$— wherein p, q and r are as defined above.

Chemiluminescent particles are particles that have associated therewith a chemiluminescent compound. The phrase "associated therewith" as used herein means that a compound such as, for example, a chemiluminescent compound and a particle may be associated by direct or indirect bonding, adsorption, absorption, incorporation, or solution, for example. Examples of chemiluminescent compounds that may be utilized are those set forth in U.S. Pat. Nos. 5,340,716 and 6,251,581, the relevant disclosures of which are incorporated herein by reference. In some examples in accordance with the principles described herein, the chemiluminescent compound is a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". In some examples, the chemiluminescent compounds are those that react with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, and luminol. Examples of such chemiluminescent compounds that may be utilized are those set forth in U.S. Pat. No. 5,709,994, the relevant disclosure of which is incorporated herein by reference.

Sensitizer particles are particles that have associated therewith a sensitizer compound, which includes, but is not limited to, a photosensitizer compound. Examples of sensitizer compounds that may be utilized are those set forth in U.S. Pat. Nos. 5,340,716 and 6,251,581, the relevant disclosures of which are incorporated herein by reference.

A photosensitizer is a sensitizer for generation of singlet oxygen usually by excitation with light. In some examples, the photosensitizer absorbs at a longer wavelength than the chemiluminescent compound and has a lower energy triplet than the chemiluminescent compound. The photosensitizer can be photoactivatable (e.g., dyes and aromatic compounds). The photosensitizer is usually a compound comprised of covalently bonded atoms, usually with multiple conjugated double or triple bonds. The compound should absorb light in the wavelength range of 200-1100 nm, usually 300-1000 nm, preferably 450-950 nm. Typical photosensitizers include, but are not limited to, acetone, benzophenone, 9-thioxanthone, eosin, 9,10-dibromoanthracene, methylene blue, metalloporphyrins (e.g., hematoporphyrin), phthalocyanines, chlorophylls, rose bengal, buckminsterfullerene, for example, and derivatives of these compounds. Examples of other photosensitizers are enumerated in N. J. Turro, "Molecular Photochemistry", page 132, W. A. Benjamin Inc., N.Y. 1965. The photosensitizer assists photoactivation where activation is by singlet oxygen. Usually, the photosensitizer absorbs light and the thus formed excited photosensitizer activates oxygen to produce singlet oxygen, which reacts with the chemiluminescent compound to give a metastable luminescent intermediate.

In some examples in accordance with the principles described herein, the compound has the formula:

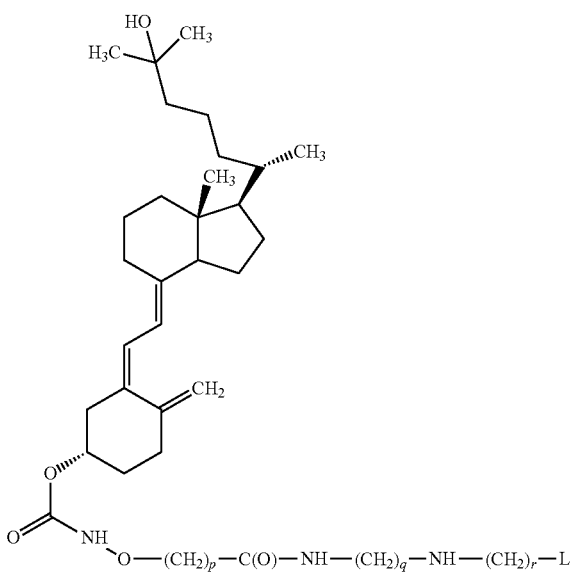

wherein L, p, q and r are as defined above.

In some examples in accordance with the principles described herein, the compound has the formula:

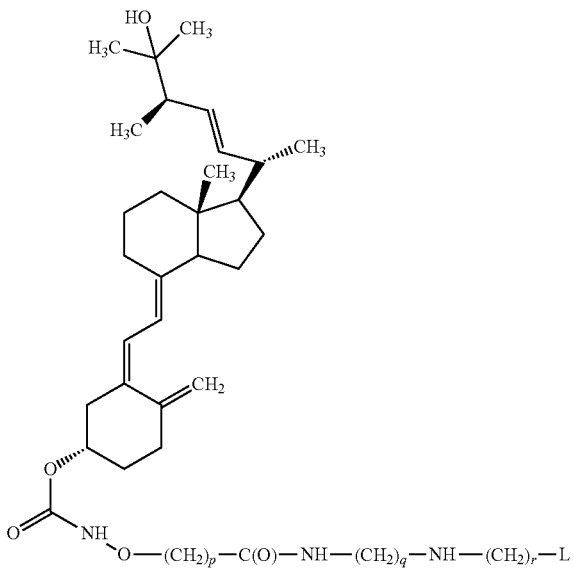

wherein L, p, q and r are as defined above.

Preparation of Compounds

Figure 2:
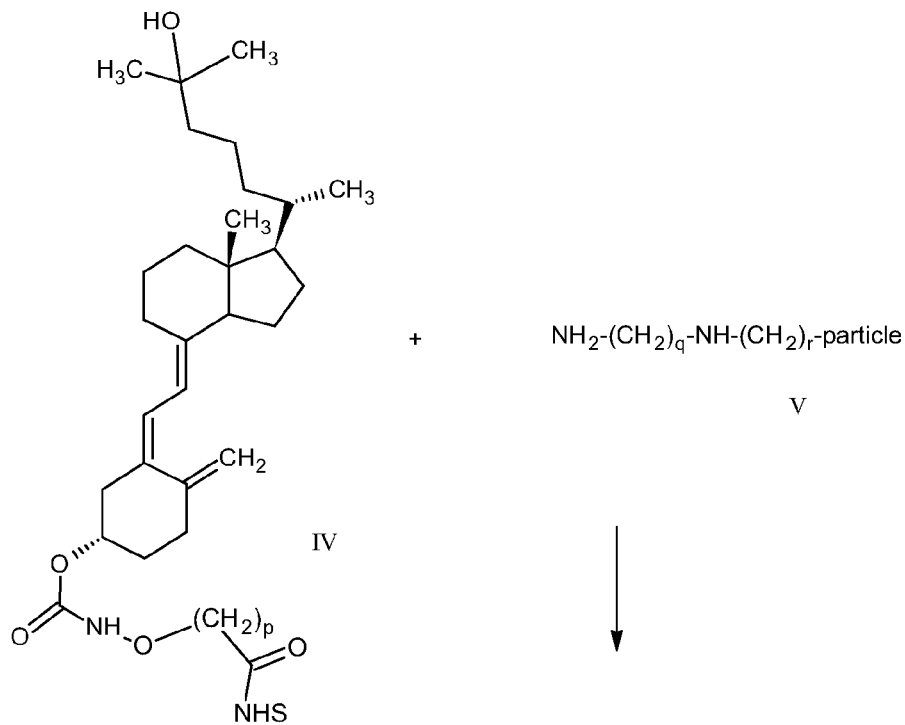
FIG. 2 is a schematic diagram of a synthesis of compounds in accordance with examples in accordance with the principles described herein.
Figure 2:
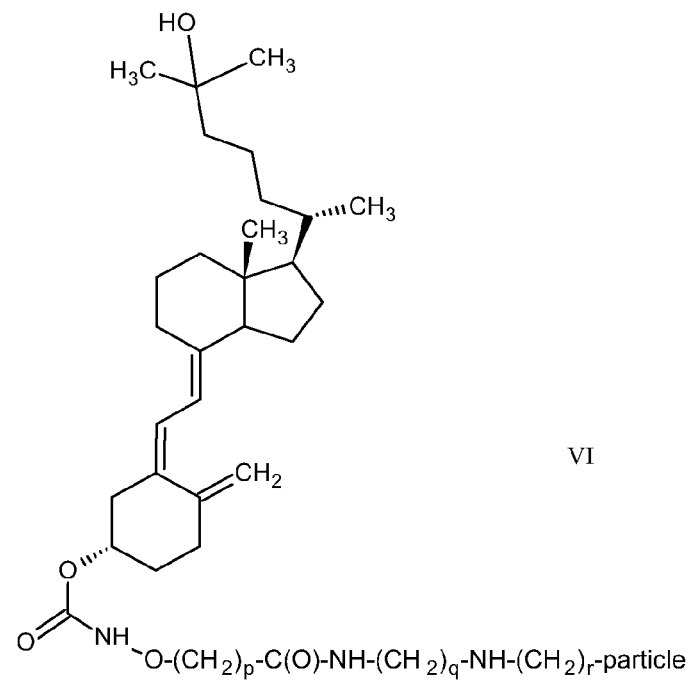

Examples of methods of preparing compounds in accordance with the principles described herein are described, by way of illustration and not limitation, with reference to FIGS. 1 and 2. Other approaches may be employed to form the compounds consistent with the principles described herein. Referring to FIG. 1, 25-OH VD$_3$(I) is treated to form succinimidyl carbonate derivative II. For example, I may be combined with disuccinimidyl carbonate in the presence of a base in an anhydrous polar organic solvent. The base may be, for example, triethylamine or diisopropylethylamine. The anhydrous polar organic solvent may be, for example, acetonitrile, dichloromethane, tetrahydrofuran (THF), dimethylformamide (DMF) or dimethylsulfoxide (DMSO). The temperature during the reaction is about 18° C. to about 25° C., or about room temperature. The reactants are subjected to agitation during the reaction by stirring or shaking, for example. The time period of the reaction is about 2 hours to about 24 hours, or about 15 to about 21 hours, or about 18 hours.

Carbamate III (25-OH vitamin D$_3$ 3-carbamate, p=1) may be prepared from succinimidyl carbonate derivative II by, for example, combining II with a suspension of carboxymethoxylamine hemihydrochloride (CMO) in the presence of a base in an anhydrous polar organic solvent. The base may be, for example, triethylamine or diisopropylethylamine. The anhydrous polar organic solvent may be, for example, DMF or DMSO. The reaction vessel containing the above reactants is held in a heating bath at a heating bath temperature during the reaction of about 18° C. to about 25° C., or about 22° C. The reactants are subjected to agitation during the reaction by stirring or shaking, for example. The time period of the reaction is about 15 to about 21 hours, or about 18 hours. The organic solvent is removed by evaporation, which may be accelerated by subjecting the contents of the reaction vessel to a vacuum. The residue may be combined with a polar organic solvent such as, for example, ethyl acetate or dichloromethane and then washed with an aqueous solution of an inorganic salt such as, for example, brine or sodium bicarbonate solution. The organic phase may be dried by, for example, mixing with an anhydrous inorganic salt such as, sodium sulfate or magnesium sulfate, for example. Following drying, the organic phase may be treated to separate any solid material by subjecting the organic phase to, for example, filtration or decantation. The organic solvent is removed by evaporation, which may be accelerated by subjecting the contents of the reaction vessel to a vacuum. The resulting dry product may be purified by chromatographic means such as, for example, high performance liquid chromatography (HPLC), reverse phase liquid chromatography (RPLC), high turbulence liquid chromatography (HTLC), or gas chromatography. The product may be stored in an anhydrous polar organic solvent such as, for example, DMSO or DMF.

Carbamate III may be activated for coupling to a linking group of a solid support such as, for example, a particle. In one example in accordance with the principles described herein, carbamate III is activated by formation of sulfo-NHS ester IV. The reaction is carried out by combining carbamate III with an activation agent such as, for example, sulfo-NHS, in the presence of, for example, 1-ethyl-3-(3-dimethylaminopropyl)carbodiimide (EDAC) in an anhydrous polar organic medium such as, for example, DMSO, at a temperature of about 15° C. to about 40° C., or about 20° C. to about 30° C., or at ambient temperature for a period of about 10 hours to about 25 hours, or about 12 hours to about 20 hours, or about 18 hours. The medium is subjected to agitation such as by rotating or stirring, for example.

Referring to FIG. 2, a particle such as, for example, a latex particle (designated EPRM in this example) having incorporated therein a chemiluminescent compound (dye) and having an inner aminodextran layer and an outer dextran aldehyde layer is prepared by a procedure similar to that described in U.S. Pat. No. 7,179,660, the relevant disclosure of which is incorporated herein by reference. Aldehyde groups on the outer dextran aldehyde layer are reacted with ethylene diamine under reductive amination conditions to form reagent V (EPRM-EDA), which is a particle reagent having pendant moieties comprising an ethylene chain and a terminal amine group. The reductive amination conditions include the use of a reducing agent such as, for example, a metal hydride (e.g., sodium borohydride or potassium borohydride), sodium cyanoborohydride, or sodium triacetoxyborohydride. The reaction is carried out in an aqueous medium at a temperature during the reaction of about 20° C. to about 100° C., or about 30° C. to about 50° C., for a period of about 1 hour to about 48 hours, or about 5 hours to about 24 hours. The point of linkage of the pendant moieties with the outer dextran aldehyde layer comprises a secondary amine linkage.

Sulfo-NHS ester IV (in an anhydrous polar organic solvent such as, for example, DMSO or DMF) is combined with particle reagent V (in an anhydrous polar organic solvent such as, for example, DMSO or DMF, with a surfactant such as, for example, GAFAC® or TWEEN® 20). The reaction mixture is subjected to agitation by, for example, stirring or shaking. The temperature during the reaction is about 18° C. to about 25° C., or about room temperature. The reactants are subjected to agitation during the reaction by stirring or shaking, for example. The time period of the reaction is about 2 hours to about 24 hours, or about 15 to about 21, for example. The resulting particle (VI) may be subjected to one or more washing and purification techniques such as, for example, diafiltration and sonication, for example.

Vitamin $D_2$ derivatives in accordance with the principles described herein may be prepared in a manner similar to that described above for the preparation of vitamin $D_3$ derivatives in accordance with the principles described herein.

General Description of Assays for Vitamin D Utilizing the Present Compounds

Some examples in accordance with the principles described herein are directed to methods of determining one or both of the presence and the amount of vitamin D in a sample suspected of containing vitamin D and may be referred to herein as "assays for vitamin D." In the assay a combination in a medium is provided that comprises the sample, a compound as described above comprising a member of a signal producing system and a specific binding member for vitamin D. As used herein in reference to assays, the term "vitamin D" refers to one or more of 25-hydroxycholecalciferol (also referred to as calcidiol, calcifediol, 25-hydroxycholecalciferol, or 25-hydroxyvitamin D (abbreviated 25(OH)D); calcidiol; 1,25-dihydroxyvitamin $D_3$ (calcitriol; 1,25(OH)$_2D_3$); 1,25-dihydroxy vitamin $D_4$; 1,25-dihydroxy vitamin $D_5$; and 1,25-dihydroxy vitamin $D_6$; including metabolites of all of the above.

One particular example in accordance with the principles described herein is directed to methods of determining one or both of the presence and the amount of vitamin D in a sample suspected of containing vitamin D. A combination is provided that comprises the sample, a specific binding member for vitamin D and a compound of the formula:

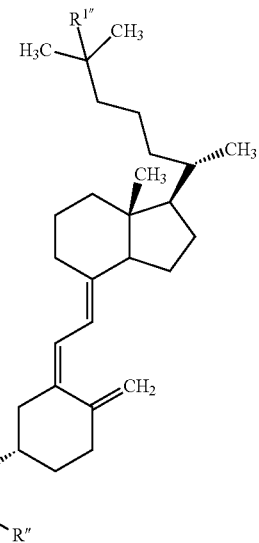

or a compound of the formula:

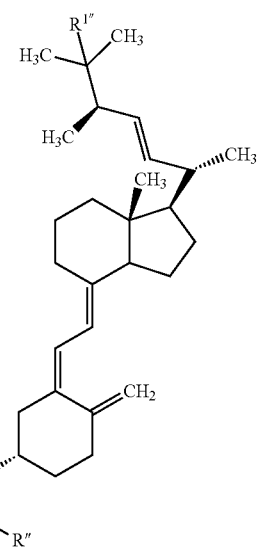

wherein: R" is —NH—O-A"—$R^{2'}$, wherein $R^{2'}$ is a member of a signal producing system as defined above and A" is a linking group as defined above, and R" is H or OH. The combination is subjected to conditions for binding of the compound to the specific binding member to form a complex, and the amount of the complex is measured. The amount of the complex is related to the presence and/or amount of vitamin D in the sample.

The specific binding member is a member of a specific binding pair, which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, for example, are not immunological pairs but are included within the scope of the term "sbp member."

Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

In some examples of assays in accordance with the principles described herein, the specific binding member for vitamin D is an antibody for vitamin D, which may be a complete immunoglobulin molecule or a fragment thereof. Antibodies include various classes and isotypes, such as IgA, IgD, IgE, IgG1, IgG2a, IgG2b and IgG3, and IgM, for example. Fragments thereof may include Fab, Fv and F(ab')$_2$, Fab', and the like. In addition, aggregates, polymers, and conjugates of immunoglobulins or their fragments can be used where appropriate so long as binding affinity for vitamin D is retained. Antibodies for vitamin D may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

The sample to be analyzed is one that is suspected of containing vitamin D. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum. Non-biological samples including, but not limited to, waste streams, for example, may also be analyzed using compounds in accordance with the principles described herein.

The sample can be prepared in any convenient medium, which may be, for example, an assay medium, which is discussed more fully hereinbelow. In some instances a pretreatment may be applied to the sample such as, for example, to lyse blood cells. In some examples, such pretreatment is performed in a medium that does not interfere subsequently with an assay.

The combination in the medium is subjected to conditions for binding of the compound to the specific binding member for vitamin D to form a complex. The amount of the complex is measured where the amount of the complex is related to one or both of the presence and amount of vitamin D in the sample.

An assay for vitamin D can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example.

One general group of immunoassays includes immunoassays using a limited concentration of a compound in accordance with the principles described herein. Another group of immunoassays involves the use of an excess of one or more of the principal reagents such as, for example, an excess of a compound in accordance with the principles described herein. Another group of immunoassays includes separation-free homogeneous assays in which a labeled reagent in accordance with the principles described herein modulates the label signal upon binding of a compound in accordance with the principles described herein to a specific binding member for vitamin D, thus competing with vitamin D that may be present in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of the present conjugate upon the binding of vitamin D analyte. Such assays include, for example, optical immunosensor assays, acoustic immunosensor assays, semiconductor immunosensor assays, electrochemical transducer immunosensor assays, potentiometric immunosensor assays, amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for vitamin D bound thereto is contacted with a medium containing the sample suspected of containing vitamin D and a labeled compound in accordance with the principles described herein. Vitamin D in the sample competes, for binding to the vitamin D antibody, with the compound in accordance with the principles described herein bearing a detectable label. After separating the support and the medium, the label activity of the support or the medium is determined by conventional techniques and is related to the amount of vitamin D analyte in the sample.

In some examples, a sample to be analyzed is combined in an assay medium with an antibody for vitamin D and labeled compound in accordance with the principles described herein. The medium is examined for one or both of the presence and amount of a complex comprising the labeled compound and the antibody for vitamin D where the presence and/or the amount of such complex indicates the presence and/or amount of vitamin D in the sample.

The assays are normally carried out in an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5, for example. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include, by way of illustration and not limitation, borate, phosphate, carbonate, tris, barbital, PIPES, HEPES, MES, ACES, MOPS, and BICINE, for example. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as, for example, albumins; organic solvents such as, for example, formamide; quaternary ammonium salts; polyanions such as, for example, dextran sulfate; binding enhancers, for example, polyalkylene glycols; polysaccharides such as, for example, dextran or trehalose. The medium may also comprise agents for preventing the formation of blood clots. Such agents are well known in the art and include, but are not limited to, EDTA, EGTA, citrate, heparin, for example. The medium may also comprise one or more preservatives such as, but not limited to, sodium azide, neomycin sulfate, PROCLIN® 300, Streptomycin, for example. The medium may additionally comprise one or more surfactants. Any of the above materials, if employed, is present in a concentration or amount sufficient to achieve the desired effect or function.

One or more incubation periods may be applied to the medium at one or more intervals including any intervals between additions of various reagents employed in an assay including those mentioned above. The medium is usually incubated at a temperature and for a time sufficient for binding of various components of the reagents and binding of vitamin D in the sample to occur. Moderate temperatures are normally employed for carrying out the method and usually constant temperature, preferably, room temperature, during the period of the measurement. In some examples, incubation temperatures range from about 5° to about 99° C., or from about 15° C. to about 70° C., or from about 20° C. to about 45° C., for example. The time period for the incubation, in some examples, is about 0.2 seconds to about 24 hours, or about 1 second to about 6 hours, or about 2 seconds to about 1 hour, or about 1 minute to about 15 minutes, for example. The time period depends on the temperature of the medium and the rate of binding of the various reagents, which is determined by the association rate constant, the concentration, the binding constant and dissociation rate constant.

In an example of a method for determining vitamin D in a sample suspected of containing vitamin D, a combination is provided in a medium where the combination includes the sample, an antibody for vitamin D, and a labeled compound in accordance with the principles described herein where the label is a poly(amino acid) label or a non-poly(amino acid) label. The medium is examined for one or both of the presence and amount of one or both of a complex comprising vitamin D and the antibody for vitamin D or a complex comprising the labeled compound and antibody for vitamin D. The presence and/or the amount of one or both of the complexes indicates the presence and/or amount of vitamin D in the sample.

Some known assays utilize a signal producing system (sps) that employs first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light or an activated product, which results in activation of another member of the sps.

In some embodiments of assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member, i.e., the amount of sps member bound or not bound to the vitamin D analyte being detected or to a compound in accordance with the principles described herein. In some examples in accordance with the principles described herein, one of either the sensitizer reagent or the chemiluminescent reagent comprises the present compound reagent.

In a particular example, an induced luminescence immunoassay may be employed. The induced luminescence immunoassay is referred to in U.S. Pat. No. 5,340,716 (Ullman), which disclosure is incorporated herein by reference. In one approach, the assay uses a particle having associated therewith a photosensitizer where a compound in accordance with the principles described herein is bound to the particle (particle-compound reagent). The chemiluminescent reagent comprises an antibody for vitamin D. The vitamin D analyte competes with the particle-compound reagent for binding to the antibody for vitamin D. If the vitamin D analyte is present, the fewer is the number of molecules of particle-compound reagent that come into close proximity with the chemiluminescent reagent. Therefore, there will be a decrease in the assay signal. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of vitamin D analyte present in the sample.

In another particular example of an induced luminescence immunoassay, the assay uses a particle having associated therewith a chemiluminescent compound where a compound in accordance with the principles described herein is bound to the particle (particle-compound reagent). The photosensitizer reagent comprises an antibody for vitamin D. The vitamin D analyte competes with the particle-compound reagent for binding to the antibody for vitamin D. If the vitamin D analyte is present, the fewer is the number of molecules of particle-compound reagent that come into close proximity with the photosensitizer reagent. Therefore, there will be a decrease in the assay signal. The photosensitizer generates singlet oxygen and activates the chemiluminescent compound of the particle-compound reagent when the two labels are in close proximity. The activated chemiluminescent compound subsequently produces light. The amount of light produced is related to the amount of the complex formed, which in turn is related to the amount of vitamin D analyte present in the sample.

In another particular example of an induced luminescence assay, a photosensitizer particle is employed that is conjugated to a binding partner for a small molecule such as, for example, avidin or streptavidin (which are binding partners for biotin). A compound in accordance with the principles described herein that comprises biotin (compound-biotin reagent) is also employed. A chemiluminescent reagent that comprises a specific binding member for vitamin D is employed as part of the detection system. The reaction medium is incubated to allow the avidin or streptavidin of the photosensitizer particles to bind to the compound-biotin reagent by virtue of the binding between avidin and biotin and to also allow the specific binding member for the vitamin D that is part of the chemiluminescent reagent to bind to the vitamin D analyte or to the compound in accordance with the principles described herein that is now attached to the photosensitizer particles. Then, the medium is irradiated with light to excite the photosensitizer, which is capable in its excited state of activating oxygen to a singlet state. Because less of the chemiluminescent reagent is now in close proximity to the photosensitizer because of the presence of the vitamin D analyte, there is less activation of the chemiluminescent reagent by the singlet oxygen and less luminescence. The medium is then examined for the presence and/or the amount of luminescence or light emitted, the presence thereof being related to the presence and/or amount of the vitamin D analyte where a decrease in signal is observed in the presence of the vitamin D analyte.

In another particular example of an induced luminescence assay, a photosensitizer particle is employed that is conjugated to a binding partner for a small molecule such as, for example, avidin or streptavidin (which are binding partners for biotin). A conjugate reagent comprises a specific binding member for vitamin D conjugated to biotin. A compound in accordance with the principles described herein is employed where the compound is attached to a chemiluminescent particle (chemiluminescent-compound reagent) is also employed. The reaction medium is incubated to allow the avidin or streptavidin of the photosensitizer particles to bind to the antibody-biotin reagent by virtue of the binding between avidin and biotin and to also allow the specific binding member for the vitamin D to bind to vitamin D if present in the sample and to the compound in accordance with the principles described herein that is part of the chemiluminescent-compound reagent. Then, the medium is irradiated with light to excite the photosensitizer, which is capable in its excited state of activating oxygen to a singlet state. Because less of the chemiluminescent-compound reagent is now in close proximity to the photosensitizer because of the presence of the vitamin D analyte, there is less activation of the chemiluminescent reagent by the singlet oxygen and less luminescence. The medium is then examined for the presence and/or the amount of luminescence or light emitted, the presence thereof being related to the presence and/or amount of the vitamin D analyte where a decrease in signal is observed in the presence of the vitamin D analyte.

The concentration of the vitamin D analyte in a sample that may be assayed generally varies from about $10^{-5}$ to about $10^{-17}$ M, or from about $10^{-6}$ to about $10^{-14}$ M, for example. Considerations such as whether the assay is qualitative, semiquantitative or quantitative (relative to the amount of the vitamin D analyte present in the sample), the particular detection technique and the expected concentration of the vitamin D analyte normally determine the concentrations of the various reagents.

The concentrations of the various reagents in the assay medium will generally be determined by the concentration range of interest of the vitamin D analyte, the nature of the assay, and the like. However, the final concentration of each of the reagents is normally determined empirically to optimize the sensitivity of the assay over the range of interest. That is, a variation in concentration of vitamin D analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Examination Step

In a next step of an assay method, the medium is examined for the presence of a complex comprising the vitamin D analyte and antibody for vitamin D and/or a complex comprising a compound reagent in accordance with the principles described herein and antibody for vitamin D. The presence and/or amount of one or both of the complexes indicates the presence and/or amount of the vitamin D analyte in the sample.

The phrase "measuring the amount of a vitamin D analyte" refers to the quantitative, semiquantitative and qualitative determination of vitamin D. Methods that are quantitative, semiquantitative and qualitative, as well as all other methods for determining the vitamin D analyte, are considered to be methods of measuring the amount of the vitamin D analyte. For example, a method, which merely detects the presence or absence of the vitamin D analyte in a sample suspected of containing the vitamin D analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the vitamin D analyte in the sample. The particular mode of detection depends on the nature of the signal producing system. As discussed above, there are numerous methods by which a label of a signal producing signal can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C., for example. In one approach standard curves are formed using known concentrations of vitamin D analyte. Calibrators and other controls may also be used.

Luminescence or light produced from any label can be measured visually, photographically, actinometrically, spectrophotometrically, such as by using a photomultiplier or a photodiode, or by any other convenient means to determine the amount thereof, which is related to the amount of vitamin D analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

Kits Comprising Reagents for Conducting Assays

A reagent comprising a compound in accordance with the principles described herein attached to a member of a signal producing system, which may also comprise a support, and other reagents for conducting a particular assay for a vitamin D analyte may be present in a kit useful for conveniently performing an assay for the determination of a vitamin D analyte. In some embodiments a kit comprises in packaged combination a biotin-binding partner such as, for example, avidin or streptavidin, associated with a particle, biotinylated compound in accordance with the principles described herein and a labeled antibody for the vitamin D analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional specific binding pair members, signal producing system members, and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay using a compound reagent in accordance with the principles described herein. The kit can further include a written description of a method utilizing reagents that include a compound reagent in accordance with the principles described herein.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

EXAMPLES

Unless otherwise indicated, materials in the experiments below may be purchased from the Sigma-Aldrich Chemical Corporation (St. Louis Mo.) or Fluka Chemical Corporation (Milwaukee Wis.). Parts and percentages disclosed herein are by weight to volume unless otherwise indicated.

Definitions
    mg=milligram
    g=gram(s)
    ng=nanogram(s)
    mL=milliliter(s)
    μL=microliter(s)
    μmol=micromolar
    ° C.=degrees Centigrade
    min=minute(s)
    sec=second(s)
    hr=hour(s)
    w/v=weight to volume
    TLC=thin layer chromatography
    HPLC=high performance liquid chromatography
    EtOAc=ethyl acetate
    DMF=dimethylformamide
    DMSO=dimethylsulfoxide
    MeOP=1-methoxy-2-propanol
    MES=2-(N-morpholino)ethanesulfonic acid
    DI=distilled
    UPA=Ultra Particle Analyzer
    LOCI=luminescent oxygen channeling immunoassay
    BSA=bovine serum albumin
    BGG=bovine gamma globulin
    mIgG=mouse immunoglobulin
    MS=mass spectrometry Preparation of EPRM-EDA Beads EPRM beads (2000 mg, 20.0 mL) are added to a 40-mL vial. The EPRM beads are prepared by a procedure similar to that described in U.S. Pat. No. 7,179,660 and the chemiluminescent compound is 2-(4-(N,N, di-tetradecyl)-anilino-3-phenyl thioxene with europium chelate. EDA (800 mg, 890 μL) is combined with 10 mL MES pH 6 buffer (the "Buffer") and about 4.2 mL 6N HCl. The pH of the mixture is, or is adjusted to be, about 6.9. The EDA solution is added to the EPRM beads with vortexing and the mixture is rocked at room temperature for 15 minutes. Sodium cyanoborohydride (400 mg) is combined in a 15 mL vial with 10 mL DI water and the combination is added to the bead mixture from above. The mixture is shaken at 37° C. for 18-20 hours. The beads are transferred to six 40 mL centrifuge tubes. MES buffer is added to bring the volume to 35 mL and the mixture is centrifuged at 19,000 rpm for 30 min. The supernatant is decanted and the beads are re-suspended in 2 mL of the Buffer with a stir-rod and additional Buffer is added to 35 mL. The mixture is sonicated at 18 Watts power for 30 sec, using ice to keep the mixture cold. The wash/sonication step is performed 4 times to remove all activation chemical. After the last MES Buffer centrifugation, 2 mL of the Buffer containing 5% MeOP and 0.1% Tween® 20 (the "second Buffer") is added to the tubes for the re-suspension step. Additional second buffer is added to 35 mL before sonication. The bead suspension is centrifuged at 19,000 rpm for 30 min. The supernatant is discarded. The final sonication used 12 mL of the second Buffer in each tube to give a 25 mg/mL dilution. Particle size is 277 nm as determined on a UPA instrument.

The EPRM chemibead is prepared in a manner similar to the method described in U.S. Pat. No. 6,153,442 and U.S. Patent Application Publication No. 20050118727A, the relevant disclosures of which are incorporated herein by reference. The EPRM chemibead comprises an aminodextran inner layer and a dextran aldehyde outer layer having free aldehyde functionalities. See, for example, U.S. Pat. Nos. 5,929,049, 7,179,660 and 7,172,906, the relevant disclosures of which are incorporated herein by reference. The reaction is carried out at a temperature of about 0 to about 40° C. for a period of about 16 to about 64 hours at a pH of about 5.5 to about 7.0, or about 6, in a buffered aqueous medium employing a suitable buffer such as, for example, MES. The reaction is quenched by addition of a suitable quenching agent such as, for example, carboxymethoxyamine hemihydrochloride (CMO), and subsequent washing of the particles.

Aldehyde groups on the outer dextran aldehyde layer are reacted with ethylene diamine under reductive amination conditions to form reagent EPRM-EDA having pendant moieties comprising an ethylene chain and a terminal amine group. The reductive amination conditions include the use of a reducing agent such as, for example, a metal hydride. The reaction is carried out in an aqueous medium at a temperature during the reaction of about 20° C. to about 100° C. for a period of about 1 hour to about 48 hours.

Synthesis of 25-OH Vitamin $D_3$ 3-carbamate (25-OH Vitamin $D_2$ 3-carbamate)

Referring to FIG. 1, a mixture of 22 mg (55 μmol) 25-OH $VD_3$ (I) purchased from ChemReagents.com, Sugarland Tex., 100 mg (420 μmol) disuccinimidyl carbonate (DSC), 100 μL triethylamine in 1 mL anhydrous acetonitrile in a 5-ml flask (covered with foil) was stirred at room temperature for 18 hr under nitrogen to prepare activated 25-OH $VD_3$ (II). TLC (EtOAc:Hexane=2:1) showed no starting material left. A suspension was prepared by adding 150 mg of carboxymethoxylamine hemihydrochloride (CMO), 0.3 ml triethylamine and 1 ml DMF to a 10 ml flask. A solution containing activated 25-OH $VD_3$ was added dropwise to the CMO suspension with stirring, which was continued for another 18 hr. Vacuum was applied to remove the solvents as much as possible (the heating bath temperature should not be over 50° C.). EtOAc (25 ml) was added to the residue, which was washed three times with 2 ml brine. The organic phase was dried with anhydrous $Na_2SO_4$ and was filtered; solvent was removed using rotavap. Crude product (42 mg) was obtained after drying and was purified by HPLC. Pure product (III) (p=1) (24 mg) was obtained after being dried under high vacuum. The product was dissolved into 1.2 ml anhydrous DMSO. Aliquots were transferred into vials, which were kept at −70° C.

A method similar to that described above was employed to prepare 25-OH Vitamin $D_2$ 3-carbamate using 25-OH $VD_2$.

Synthesis of 25-OH Vitamin $D_3$ 3-succinate (25-OH Vitamin $D_2$ 3-succinate)

A mixture of 14.4 mg (35.4 μmol) 25-OH $VD_3$, 8.2 mg (90 μmol) succinic anhydride, 8.2 mg imidazole in 1 mL anhydrous dichloromethane in a 5-ml flask was stirred at room temperature for 24 hr under nitrogen. TLC (EtOAc:Hexane=2:1) showed no starting material left. Solvent was removed under vacuum using a heating bath under 50° C. EtOAc was added to the residue, which was then washed three times with 3×2 ml brine. The organic phase was removed with anhydrous $Na_2SO_4$ and was filtered. Solvent was removed using a rotavap and the resulting material was subjected to drying under high vacuum to give 18 mg of crude product, which was confirmed to be 25-OH Vitamin D3 3-succinate by MS.

A method similar to that described above was employed to prepare 25-OH Vitamin $D_2$ 3-succinate using 25-OH $VD_2$.

Coupling of EPRM-EDA and 25-OH Vitamin $D_3$ 3-Carbamate to Give Particle Reagent VI Referring to FIGS. 1 and 2, carbamate III (10 μL of aliquot in DMSO prepared as described above) (0.2 mg) was added to a 2-mL vial labeled 3323-064-1. EDAC (6.8 mg) and SNHS (9.4 mg) plus 2.27 mL dry DMSO (3 mg/mL) were added to a 5-mL vial labeled EDAC/SNHS. The EDAC/SNHS solution (190 μl) was added to vial 3323-064-1 (1 mg/mL) to prepare activated 25-OH vitamin $D_3$ 3-carbamate IV. The mixture was allowed to rotate at room temperature for 18 hr. A 0.4 mL aliquot of a 16% GAFAC® surfactant solution (GAF Corporation, Wayne N.J.) (0.15%) was diluted to 1.6% with 3.6 mL DI water.

Vitamin $D_3$ (8.5 mg) and 850 μl, DMSO (10 mg/mL) were combined. To a 10-mL round bottom flask (labeled 3323-064B) equipped with a stir-bar was added 2.0 mL (200MG) EPRM-EDA followed by 400 μL (4 mg) of the Vitamin $D_3$ solution from above. The mixture stirred overnight at room temperature.

To a 10-mL round bottom flask (designated 3323-64A) equipped with a stir-bar was added 2.0 mL (200 mg) EPRM-EDA (prepared as described above) followed by 260 μL 1.6% GAFAC® surfactant solution (0.15%) with moderate stirring. To a small test tube was added 504 μl, anhydrous DMSO followed by 60 μl, (0.06 mg) 3323-064-1 activated Vitamin $D_3$-3-carbamate IV prepared as described above; and the mixture was added to the EPRM-EDA bead mixture. The total DMSO content of the 3323-64A the bead suspension was 20%.

To the 10-mL round bottom flask (designated 3323-064B) was added 260 μL 1.6% GAFAC® surfactant solution (0.15%) with moderate stirring. To a small test tube was added 104 μl, anhydrous DMSO followed by 60 μl, (0.06 mg) 3323-064-1 activated vitamin $D_3$-3-carbamate IV. The DMSO/activated vitamin $D_3$-3-carbamate IV was added to the bead mixture. The combined reactants (Vitamin $D_3$/DMSO) plus added DMSO gave a 20% DMSO content to the 3323-064B bead suspension. The two reaction vessels were allowed to stir overnight at room temperature. Then, the beads were washed by means of diafiltration.

Each bead lot was taken up to 20 mL working volume with 10% MeOP/1% GAFAC®/MES pH6 buffer. The mixture was diafiltered with 5 volumes of the buffer and then sonicated with a probe sonicator at 18-21 Watts using ice to keep the mixture cold. The diafiltration/sonication continued through 50 volumes with effluent samples being taken at 35, 40, 45 and 50 volumes. The buffer was changed to LOCI Hapten Wash Buffer (50 mM HEPES, 300 mM NaCl, 1 mM EDTA, 0.01% neomycin sulfate, 0.1% TRITON® 405X and 0.15% PROCLIN® 300, pH 7.2) with 10 volumes being used. The mixture was reduced to about 7 mL and a UPA performed. Particle sizes were 3323-064A=289 nm and 3323-064B=298 nm. Percent solids were determined and both bead lots were brought up to 10 mg/mL with LOCI Hapten Wash Buffer pH7.2. Yield was as follows: 3323-064A=160.4 mg and 3323-064B=183.5 mg.

Coupling of EPRM-EDA and 25-OH Vitamin $D_2$ 3-Carbamate to Give Particle Reagent VI In a manner similar to the described above for the preparation of particle reagent VI, 25-OH Vitamin $D_2$ 3-Carbamate was coupled to EPRM-EDA to give a similar particle reagent.

Coupling of EPRM-EDA and 25-OH Vitamin $D_3$ 3-succinate

25-OH Vitamin $D_3$ 3-succinate (66 μL of aliquot in DMSO prepared as described above) (2 mg) was added to a 2-mL vial labeled 3323-026-1. EDAC (20 mg) and NHS (20 mg) plus 0.8 mL dry DMSO (25 mg/mL) were added to a 5-mL vial labeled EDAC/NHS. The EDAC/NHS solution (180 μL) was added to vial 3323-026-1 (8.1 mg/mL) to prepare activated vitamin $D_3$-3-succinate. The mixture was allowed to rotate at room temperature for 18 hr. To a 2-mL centrifuge tube 3323-026A was added 0.5 mL (50 mg) EPRM-EDA followed by 1.4 ml MES pH6 followed by (119 μL) (0.96 mg) of activated vitamin $D_3$-3-succinate (with vortexing during addition). The addition gave a 5.9% DMSO content to the beads.

To a 2-mL centrifuge tube labeled 3323-026B was added 0.5 mL (50 mg) EPRM-EDA followed by 1.4 ml MES pH6 followed by 69 μL DMSO plus 30 μL (0.24 mg) of activated Vitamin $D_3$-3-Succinate (with vortexing during addition). The addition plus the extra DMSO gave a 5% DMSO content to the beads.

Mixtures were transferred to 40-mL centrifuge tubes. MES pH6 Buffer containing 10% MeOP and 1% GAFAC® was added to bring the volume in the tubes to 35 mL. Tubes were centrifuged at 18,500 rpm for 30 minutes. Supernatant was decanted.

Beads were re-suspended in 1 mL MES Buffer mixture with a stir-rod. More MES Buffer mixture was added to bring tubes to 35 mL. Using ice to keep tubes cold, the tubes were sonicated (probe sonicator) at 18-21 Watts power for 60 seconds. The beads were centrifuged as above with a total of four MES-MeOP-GAFAC® buffer washes being performed. After the last wash, the beads were resuspended in 1 mL Hapten Wash Buffer instead of the MES Buffer mixture as above with two more washes being performed. The beads were resuspended in sufficient Hapten Wash Buffer to give a 15 mg/mL suspension. Beads were sonicated at 50% power (cup sonicator) for 60 seconds. Particle size was determined on a UPA instrument. Particle size for 3323-26A was 290 nm; particle size for 3323-26B was 275 nm. Yield was as follows: 3323-26A=33.2 mg and 3323-26B=32.3 mg.

Assay for Vitamin D Analyte

Assays were carried out on a DIMENSION® VISTA® analyzer (Siemens Healthcare Diagnostics Inc., Deerfield, Ill.) following the protocol for a LOCI assay and using sample solutions containing varying amounts of 25-hydroxyvitamin D3. In this example, the assay uses, as a chemiluminescent reagent, a label particle-conjugate ("chemibead(s)") in accordance with the principles described herein where the label of the particle-conjugate is a chemiluminescent compound contained in a latex particle. Samples were reacted first with a biotinylated antibody against 25-hydroxyvitamin D and then with chemibeads. The chemibeads bind to the fraction of the monoclonal antibody binding sites that is not occupied by analyte from the sample. Subsequently, streptavidin coupled sensitizer beads are added to the reaction mixture. This leads to the formation of chemibead/sensibead pairs whose concentration is inversely related to the concentration of 25-hydroxyvitamin D3. Upon illumination at 680 nm, the sensitizer beads generate singlet oxygen which diffuses into the chemibeads which are paired with sensibeads, reacts with the olefinic dye and triggers a chemiluminescent signal at approximately 612 nm which is inversely related to the analyte concentration.

The streptavidin-sensitizer bead ("sensibead(s)") is prepared using a method analogous to that described in U.S. Pat. Nos. 6,153,442, 7,022,529, 7,229,842 and U.S. Patent Application Publication No. 20050118727A. The photosensitizer was bis-(trihexyl)-silicon-t-butyl-phthalocyanine The concentration of sensibead reagent was 200 µg/mL in HEPES buffer, pH 8.0 containing 150 mM NaCl. The EPRM-EDA-25-OH Vitamin $D_3$ particle reagent VI prepared as described above was employed as a "chemibead reagent" at a concentration of 200 µg/mL in HEPES buffer, pH 7.2, containing 150 mM NaCl and 0.1% detergent.

The biotinylated antibody reagent is prepared using monoclonal antibody specific for 25-hydroxyvitamin D (sheep monoclonal antibody from Bioventix, Farnham, Surrey, UK) and biotinylating amine groups of the antibody by reaction with NHS-PEO4-biotin (Pierce Chemical Company, Rockford Ill.) in a manner similar to that described in U.S. Patent Application Publication No. 2009/0258435A1, the relevant portions of which are incorporated herein by reference. The biotinylated antibody reagent is prepared in HEPES buffer pH 7.2 containing 150 mM NaCl and 16 mg/mL BSA, 1 mg/mL mIgG and 2 mg/mL BGG where the concentration of biotinylated antibody reagent is 1000 ng/mL.

The assays were also carried out as above with the exception that EPRM-EDA-25-OH vitamin $D_3$ succinate particle reagent was employed in place of EPRM-EDA-25-OH Vitamin $D_3$ particle reagent VI.

At time t=zero sec, 20 µL biotinylated antibody reagent and 20 µL water were added to a reaction vessel. Sample, 12 µL, was added 21.6 seconds later, followed by 8 µL water. At t=414.0 seconds, 40 µL chemibead reagent was added followed by 20 mL of water. Sensibead reagent was then dispensed at 457.2 seconds. Measurements were taken 601.2 seconds after initiation of the reaction sequence.

The results are summarized in Table 1 below.

TABLE 1

| | kcounts | | | |
|---|---|---|---|---|
| | 25-OH-$D_3$-3-carbamate | | 25-OH-$D_3$-3-succinate | |
| Vitamin D (ng/mL) | 9.6 mg/g | 4.8 mg/g | 9.6 mg/g | 4.8 mg/g |
| 0 | 1118 | 812 | 414 | 653 |
| 2 | 1135 | 818 | 417 | 662 |
| 5 | 1128 | 813 | 410 | 654 |
| 23 | 1039 | 744 | 376 | 594 |
| 216 | 651 | 488 | 237 | 387 |
| 528 | 418 | 337 | 159 | 269 |

As can be seen from Table 1, the 25-OH-$D_3$-3-carbamate chemibead reagent in accordance with the principles described herein gave consistently higher signal counts compared to the 25-OH-$D_3$-3-succinate chemibead reagent.

All publications and patent applications cited in this specification are herein incorporated by reference as if each individual publication or patent application were specifically and individually indicated to be incorporated by reference.

It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A compound of the formula:

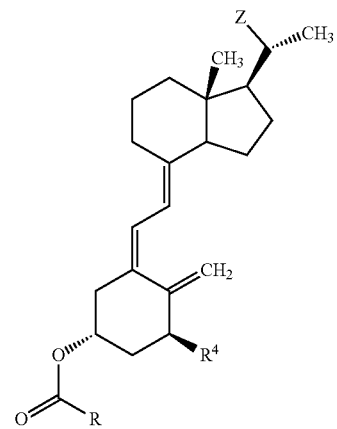

wherein:
Z is an alkyl, alkenyl or alkynyl group having 1 to 10 carbon atoms, which may be unsubstituted or one or more of which may be substituted by one or more of hydroxy, lower alkoxy, oxo, and oxime;

R is —O-succinimidyl; and

R⁴ is H, OH or lower alkoxy.

2. The compound according to claim 1 wherein Z is a branched alkyl group or a branched alkenyl group having 4 to 10 carbon atoms wherein a terminal carbon atom of the branched alkyl group or the branched alkenyl group comprises a hydroxyl.

3. A compound of the formula:

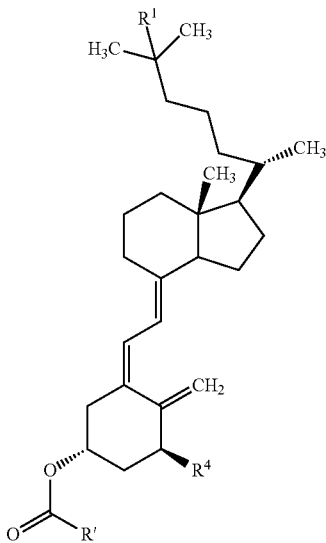

or a compound of the formula:

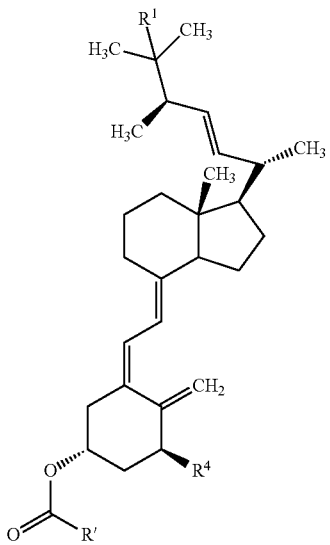

wherein:

R' is —O-succinimidyl;

R⁷ is H, OH, or protected OH; and

R⁴ is H, OH or lower alkoxy.

* * * * *